United States Patent [19]

Bonnichsen

[11] Patent Number: 5,554,134
[45] Date of Patent: Sep. 10, 1996

[54] CAP FOR AN AMPOULE OF AN INJECTION UNIT

[75] Inventor: Frits F. Bonnichsen, Lynge, Denmark

[73] Assignee: Novo Nordisk A/S, Bagsvaerd, Denmark

[21] Appl. No.: 221,277

[22] Filed: Mar. 31, 1994

Related U.S. Application Data

[63] Continuation of Ser. No. 53,501, Apr. 27, 1993, abandoned, which is a continuation of Ser. No. 768,683, filed as PCT/DK91/00281, Sep. 20, 1991 published as WO92/04927, Apr. 2, 1992, abandoned.

[30] Foreign Application Priority Data

Sep. 21, 1990 [DK] Denmark ................. 2282/90

[51] Int. Cl.⁶ ............................ A61M 5/00; A61M 5/31
[52] U.S. Cl. ..................... 604/240; 604/232; 604/415; 604/416
[58] Field of Search ....................... 604/232, 240, 604/241, 242, 200, 201, 905, 415, 411, 408, 86, 283, 192, 197; 215/317, 320, 337, 349, DIG. 3

[56] References Cited

U.S. PATENT DOCUMENTS

| | | | |
|---|---|---|---|
| 2,922,419 | 1/1960 | Bednarz. | |
| 3,375,825 | 4/1968 | Keller | 604/193 |
| 4,619,651 | 10/1986 | Kopfer et al. | 604/415 |
| 4,740,205 | 4/1988 | Seltzer et al. | 604/192 |
| 4,768,568 | 9/1988 | Fournier et al. | 141/286 |
| 4,850,970 | 7/1989 | Sutherland | 604/117 |
| 4,895,570 | 1/1990 | Larkin | 604/411 |
| 4,944,736 | 7/1990 | Holtz | 604/403 |
| 5,088,996 | 2/1992 | Kopfer et al. | 604/415 |
| 5,125,921 | 6/1992 | Duschek | 604/415 |
| 5,135,496 | 8/1992 | Vetter et al. | 604/111 |
| 5,334,162 | 8/1994 | Harris | 604/232 |

FOREIGN PATENT DOCUMENTS

| | | | |
|---|---|---|---|
| 618221 | 4/1961 | Canada | 604/200 |
| 0191122 | 8/1986 | European Pat. Off. . | |
| 0397951 | 11/1990 | European Pat. Off. . | |
| 830513 | 3/1960 | United Kingdom . | |

Primary Examiner—Randall L. Green
Assistant Examiner—V. Alexander
Attorney, Agent, or Firm—Steve T. Zelson, Esq.; James J. Harrington, Esq.

[57] ABSTRACT

A closure for the outlet end of an ampoule having a neck with an outwardly extending annular projection (30), said closure comprising a holding cap (18;61) with a skirt (35;62) with interior protrusions (38) for engagement behind the annular projection (30) of the neck, which holding cap engages a disc shape part (31) to press it sealingly against the annular projection (30). A locking ring (20;64) on the outer side of the skirt (35;62) locks projections (38) in their engagement position behind the annular projection (30). Resilient fingers (37;65) and recesses (36;66) are provided on either the skirt or the locking ring, the recesses being positioned below the fingers so that the fingers may be pushed into the recesses when the locking ring is passed over the skirt. Either the skirt (35) or the locking ring (64), which part is not provided with the fingers and recesses, is provided with an edge over which the fingers may grip irreversibly when the locking ring is mounted in position on the skirt.

4 Claims, 5 Drawing Sheets

CAP FOR AN AMPOULE OF AN INJECTION UNIT

This application is a continuation application of application Ser. No. 08/053,501, filed Apr. 27, 1993 which is now abandoned, which is a continuation of 07/768,683, filed as PCT/DK91/00281, Sep. 20, 1991, published as WO92/04927, Apr. 2, 1992, which is now abandoned.

BACKGROUND OF THE INVENTION

1. Field of the Invention

The present invention relates to an injection unit for holding of medicament, the injection unit comprising a hollow, cylindrical barrel terminating in a neck comprising an outwardly directed annular projection at its distal end, a flexible neck cap, a holding cap engaging the neck cap from the outside and comprising a proximal section in the form of a skirt having one or more interior projections at its proximal end for engagement behind the annular projection of the barrel neck, and a distal section having means for attaching a needle thereto, and a locking ring provided on the outside of the skirt at its proximal end for locking the holding cap in its engagement position.

2. Description of the Related Art

Injection units of the type mentioned above having a removable barrel neck seal allow lyophilization of the medicament contained in the barrel to be conducted in situ through the neck of the barrel.

European patent publication No. 0,191,122 discloses an injection unit in the form of a syringe and of the type mentioned in the introductory part. The syringe comprises a neck cap which extends from the proximal end of the neck of the barrel to the distal end of the holding cap and which has a passageway therethrough sealed with a cap mounted on the neck of the holding cap. The distal end of the covering cap has the form of a Luer-cone and, prior to use, the covering holding is removed and a needle is mounted on the holding cap.

In practical use, however, the above mentioned prior art syringe has been found to suffer from an essential drawback. In handling the syringe it is difficult to avoid that the holding cap is exposed to side-pressure, and as a result it frequently occurs that the holding cap slips out of its engagement position.

When the syringe is accidentally dismantled in this manner, the syringe and the medicament contained therein which may be quite expensive, must be discarded due to risk of contamination of the medicament.

Attempts have been made to overcome the above mentioned drawback by locking the holding cap in the engagement position by means of a locking ring which is mounted on the outside of the skirt of the holding cap at its proximal end following the engagement of the holding cap on the barrel neck. However, such a locking ring in combination with the prior art holding caps have proved to be insufficient as a measure of keeping the holding cap in place.

SUMMARY OF THE INVENTION

The object of the invention is to provide an injection unit for holding a medicament, the injection unit comprising a hollow, cylindrical barrel terminating in a neck comprising an outwardly directed annular projection at its distal end, a flexible neck cap, a holding cap engaging the neck cap from the outside and comprising a proximal section in the form of a skirt having one or more interior projections at its proximal end for engagement behind the annular projection of the barrel neck, and a distal section having means for attaching a needle thereto, and a locking ring provided on the outside of the skirt at its proximal end for locking the holding cap in its engagement position, in which injection unit the holding cap can be locked in a more reliable manner in the engagement position thereof.

This objective is obtained by the injection unit of the invention which is characterized in that the locking ring and the skirt of the holding cap comprise means adapted to be irreversibly engaged with each other when the locking ring is mounted in position on the skirt.

The invention is based on the recognition that the holding cap may be locked irreversibly in its engagement position by locking a locking ring irreversibly in position.

In one embodiment of the invention the skirt of the holding cap comprises a number of flexible, outwardly protruding fingers disposed at a distance from the proximal end of the skirt, and one or more recesses or openings provided in the skirt wall below the fingers and into which the fingers can be pushed.

In another embodiment of the invention the locking ring comprises a number of flexible, inwardly protruding fingers and one or more recesses or openings provided in the wall of the locking ring below the fingers and into which the fingers can be pushed, and the skirt of the holding cap is provided with one or more recesses or openings into which the fingers of the locking ring can extend.

The above mentioned embodiments of the invention function as follows:

In mounting the locking ring the fingers will be pushed into the recesses or openings provided below the fingers thus allowing the locking ring to be slipped onto the skirt of the holding cap. When the locking ring is moved into its final position, the fingers will spring back into their protruding positions, thereby irreversibly preventing the locking ring from slipping back along the skirt of the holding cap.

The above mentioned embodiments provide the advantage that the irreversible mounting of the holding cap can be performed by hand.

The holding cap may have a number of slits formed in the proximal end of its skirt. In a preferred embodiment of the invention the fingers are disposed at the distal end of said slits so as to allow the fingers to be pushed into the interior of the slits.

The holding cap and the locking ring may be constructed of a flexible thermoplastic material.

Preferably, the holding cap is injection molded in its finished form having protruding fingers. When the fingers are injection molded in its protruding positions, it is ensured that the fingers spring back to said positions upon displacement of the fingers into the skirt.

Preferably, the neck cap comprises a sealing membrane. Thus, the combination of a membrane sealing the barrel neck and the injection unit of the invention ensures to the greatest possible extent that no accidental leakage of the medicament from the injection unit or contamination of the medicament can occur as a consequence of improper or careless handling of the unit.

The neck cap may have the form of a sealing membrane bearing against the face of the barrel neck and optionally being held in place by a metal capsule, a sealing stopper provided in the inside of the barrel neck optionally having parts bearing against the face of the barrel neck and optionally having a duct formed in the proximal part thereof, or a stopper extending from the inside of the barrel neck and into the distal section of the holding cap and having a passageway formed therein.

Preferably, the neck cap is made from butyl rubber which is impermeable to gases and ensures long storage life.

In case the neck cap is designed to be penetrated by a needle prior to use, i.e. when the neck cap lacks a passageway, the neck cap preferably comprises an additional layer made from natural rubber which is characterized by having a high degree of elasticity and thus shuts tightly to the penetrated needle thereby minimizing the risk of contaminating the medicament.

The distal section of the holding cap may have the form of a Luer-cone or it may have a screw hole formed therein for mounting a threaded adaptor.

In connection with the present application the term "injection unit" may mean both a syringe and a unit for inserting into a separate injection assembly, e.g. a pen-like syringe or a delivery pump.

When the medicament is stored in its lyophilized form a so-called two-compartment injection assembly must be used, i.e. an injection assembly comprising two separate compartments for holding the medicament and the solvent, respectively, and having means for contacting and mixing the medicament and the solvent prior to use.

BRIEF DESCRIPTION OF THE DRAWINGS

The invention will now be described in further detail with reference to the drawings in which.

DESCRIPTION OF THE PREFERRED EMBODIMENTS

Figure 1:
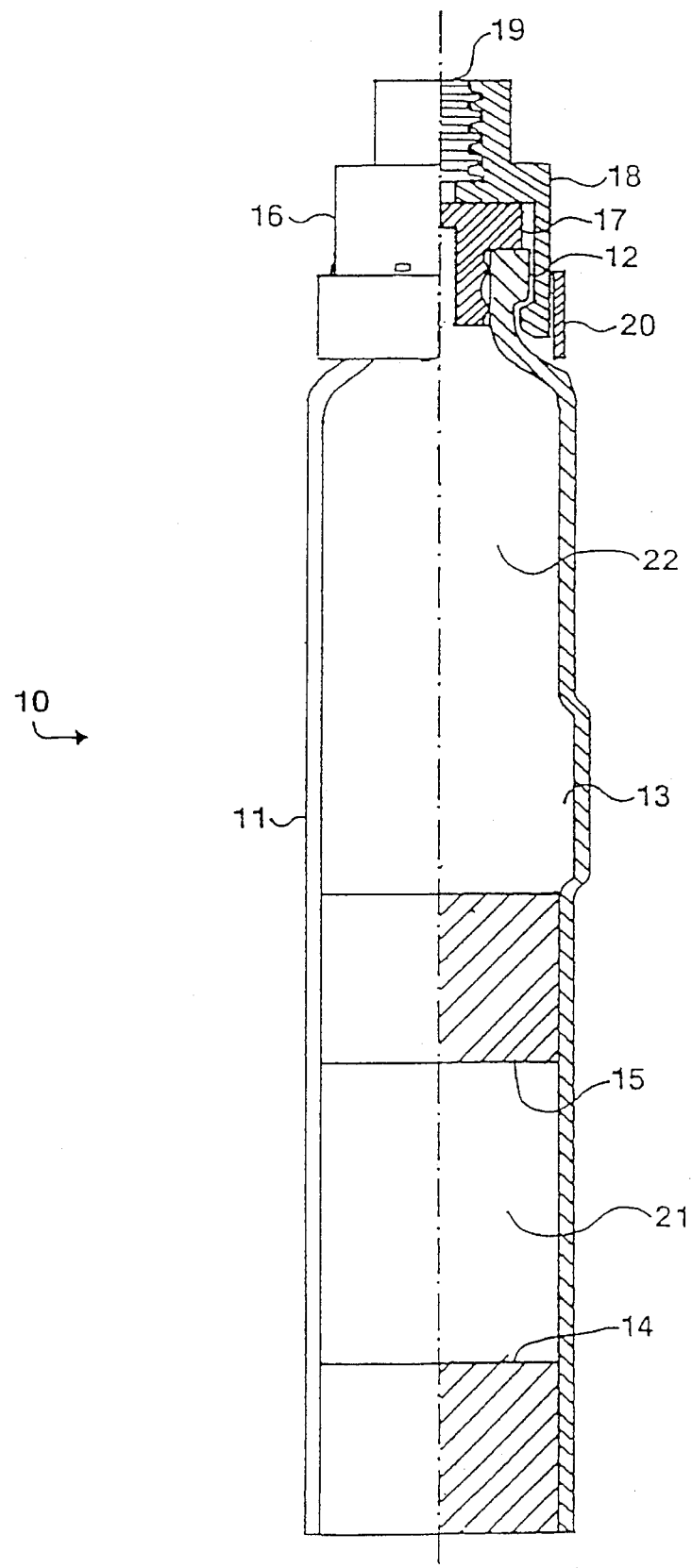
FIG. 1 shows a side view and partly a longitudinal sectional view of a preferred embodiment of an injection unit of the invention.

FIG. 1 shows an injection unit 10 of the invention in the form of a two-compartment unit for inserting into a separate injection assembly. The injection unit 10 comprises an elongated, hollow and cylindrical barrel 11 having a neck 12 at its distal end and a by-pass 13 formed in the wall thereof, a proximal piston 14, a distal piston 15, and a device 16 for sealing the neck 12 comprising a stopper 17, a holding cap 18, an adaptor 19, and a locking ring 20.

The two pistons 14 and 15 together with the sealing device 16 define a proximal 21 and a distal 22 compartment which may be used for holding a solvent and a lyophilized medicament, respectively. The medicament may be lyophilized in situ through the neck 12 of the barrel 11 before mounting the sealing device 16.

The solvent and the lyophilized medicament are mixed by pressing the pistons 14 and 15 towards the distal end of the injection unit 10. When the distal piston 15 reaches the zone defined by the by-pass, the solvent will run around the distal piston 15 and into the distal compartment 22 where it may be mixed with the lyophilized medicament. During the mixing of the solution and the medicament, a passageway connecting the distal compartment with the surrounding atmosphere should be provided so as to make ventilation of the distal compartment possible.

The ready to use medicament is discharged from the injection unit 10 by pressing the pistons 14 and 15 fully home in the barrel 11.

Figure 2:
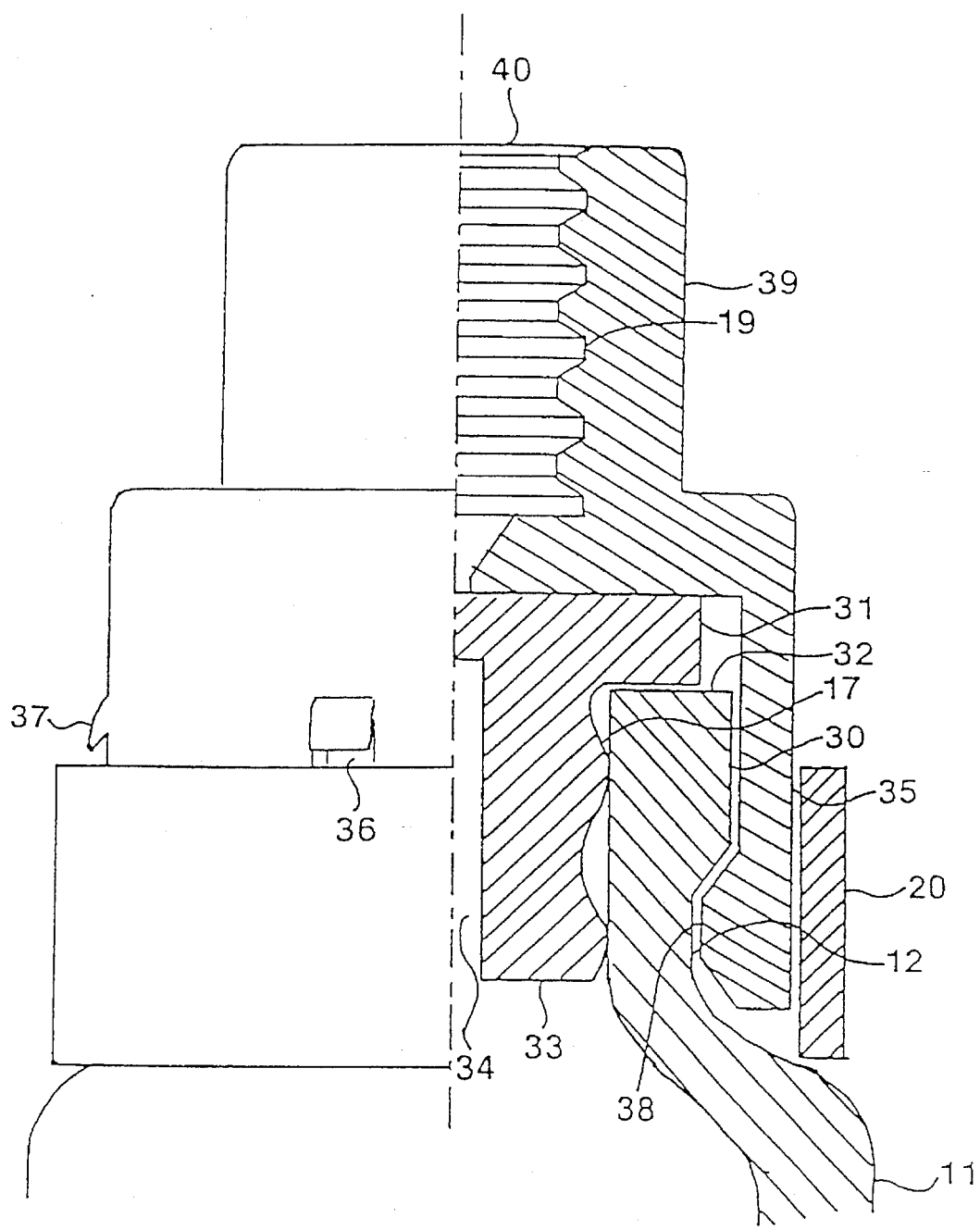
FIG. 2 shows on a larger scale a side-view and partly a longitudinal sectional view of the distal part of the injection unit shown in FIG. 1.

FIG. 2 shows the distal part of an injection unit comprising a barrel 11 terminating in a neck 12 having an annular projection 30 at its distal end. The barrel neck 12 is sealed with a stopper 17 comprising a disc-shaped part 31 bearing against part of the face 32 of the barrel neck 12, and a tubular part 33 which is inserted into the barrel neck 12 and shuts tightly to the interior of the wall of the barrel neck 12. In the proximal part of the stopper 17 a duct 34 is formed. The stopper 17 is designed to fill up the bulk of the barrel neck volume thus minimizing the amount of medicament left in the injection unit after the pistons (not shown) have been pressed fully home in the cylindrical section of the barrel 11, i.e. the wasted amount.

The stopper 17 is held in place by a holding cap 18 which also serves to press the disc-shaped part 31 of the stopper 17 tight against the face 32 of the barrel neck 12. The holding cap 18 comprises a proximal section in the form of a skirt 35 having a number of slits 36 and comprising a number of outwardly protruding, flexible fingers 37 provided at the distal end of the slits 36 and a number of interior projections 38 provided at the proximal end of the skirt 35, which projections 38 are engaged on the annular projection 30 of the barrel neck 12, and a distal section 39 having a screw hole 40 formed therein.

The screw hole 40 contains a threaded adaptor 19 holding a two-point needle (not shown). The adaptor 19 is designed so that one end of the two-point needle will penetrate the stopper 17 when the adaptor 19 is screwed into the screw hole 40 thus providing a passageway from the interior of the duct 34 to the surrounding atmosphere. The adaptor 10 is usually not mounted until the medicament is to be discharged from the injection unit.

The holding cap 18 is held in its engagement position by a locking ring 20 provided on the outside of the skirt 35 at its proximal end. The locking ring 20 is prevented from sliding back along the skirt 35 by the flexible fingers 37 provided at the distal end of the slits 36. The fingers 37 may be pushed into the interior of the slits 36 so as to allow the locking ring 20 to be mounted by slipping it onto the outside of the holding cap 18.

Figure 3:
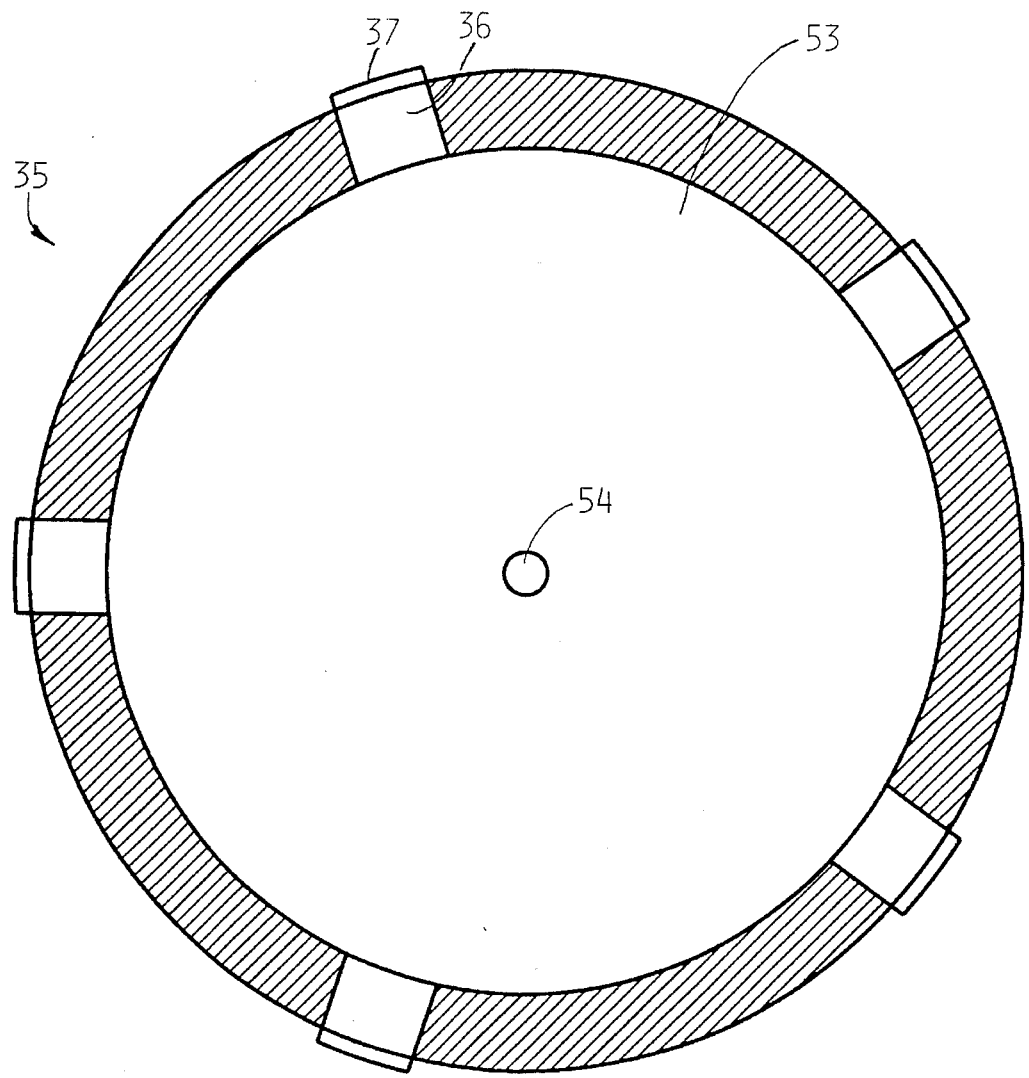
FIG. 3 shows a cross-sectional view of the proximal section of the holding cap shown in FIG. 2.

FIG. 3 shows a cross-sectional view of a skirt 50 of a holding cap. The skirt 35 has a number of slits 36 and comprises a number of outwardly protruding fingers 37 provided at the distal end of the slits 36. The skirt 35 is separated from the distal section of the holding cap by a wall 53 having a hole 54 for putting through a needle provided therein.

Figure 4:
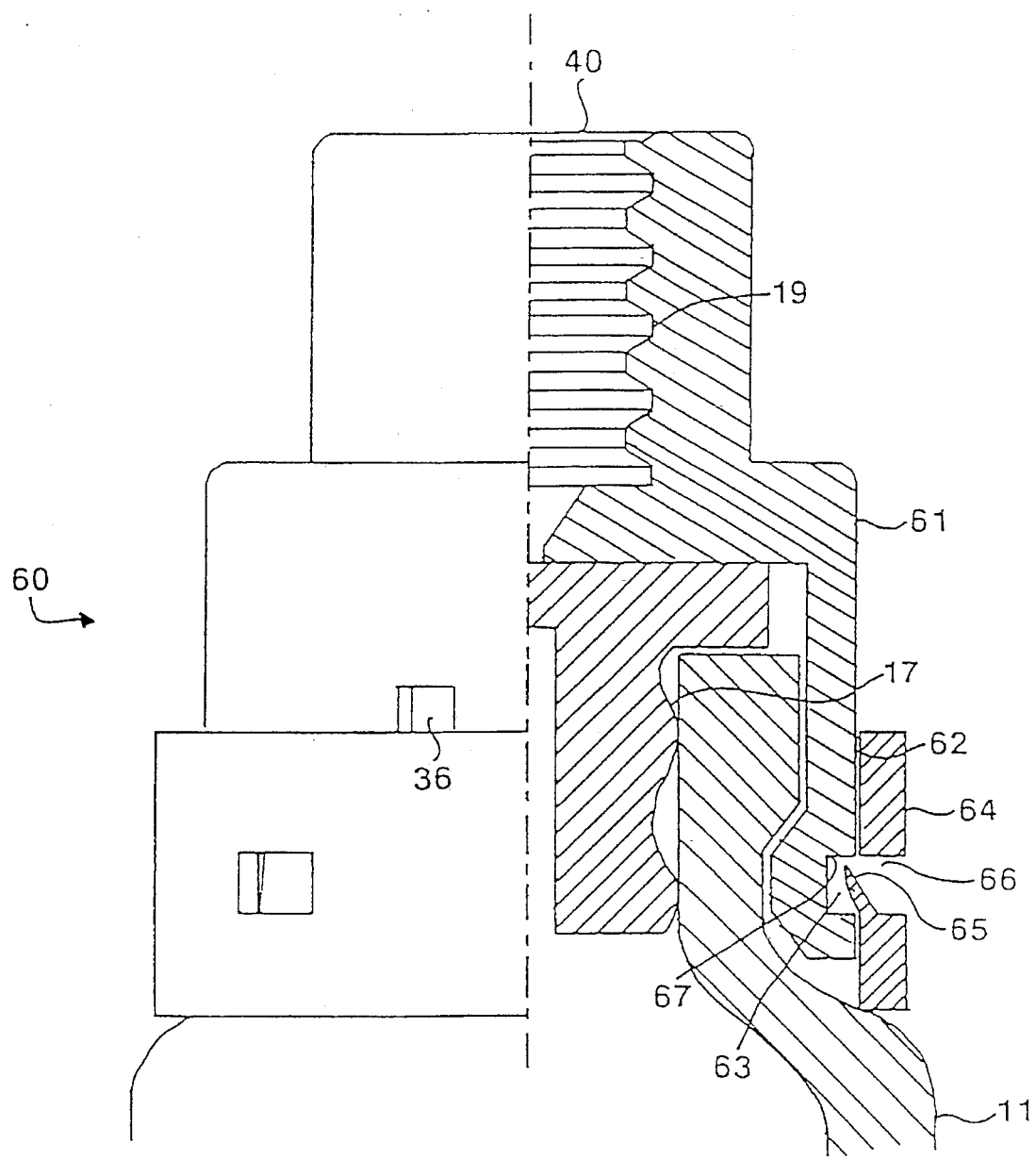
FIG. 4 shows a side-view and partly a longitudinal sectional view of another preferred embodiment of the distal part of an injection unit of the invention.

FIG. 4 shows the distal part 60 of an injection unit having a barrel 11, a stopper 17 and an adaptor 19 similar to those of the injection unit shown in FIG. 2. The stopper 17 is held in place by holding cap 61 having a skirt 62 comprising a number of slits 36 and an annular recess 63. In the distal section of the holding cap 61, a screw, hole 40 is formed.

The holding cap 61 is held in position by a locking ring 64 comprising a number of flexible, inwardly protruding fingers 65 and a number of openings 66 provided in the wall of the locking ring 64 below the fingers 65 and into which the fingers 65 can be pushed. The width of the fingers 65 and openings 66 is larger than the width of the slits 36. The locking ring 64 is prevented from sliding back along the skirt 62 by the protruding fingers 65 which run against the distal side 67 of the recess 63 of the skirt 62. When mounting the locking ring 64 on the skirt 62, the fingers 65 are pushed into the interior of the openings 66 so as to allow the locking ring 64 to be slipped onto the skirt 62.

Figure 5:
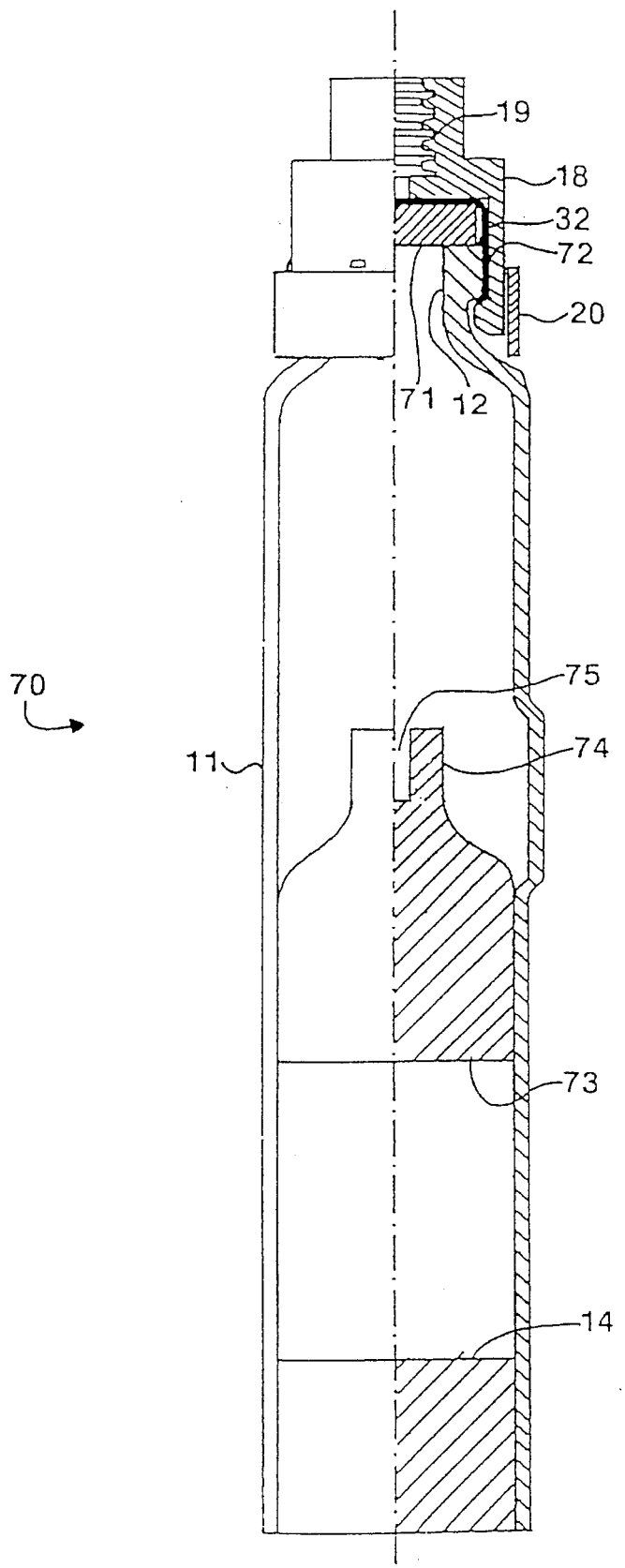
FIG. 5 shows a side-view and partly a longitudinal sectional view of an alternative embodiment of an injection unit of the invention.

FIG. 5 shows an injection unit 70 having a barrel 11, a proximal piston, 14, a holding cap 18, an adaptor 19 and a locking ring 20 similar to those of the injection unit shown in FIG. 1.

The barrel neck 12 is sealed with a membrane 71 bearing against part of the face 32 of the barrel neck 12, which membrane is held in place by a metal capsule 72, the holding cap 18 being mounted on the outside of said metal capsule 72.

The distal piston 73 comprises a tubular projection 74 provided at its distal end and having a form adapted to be introduced into the interior of the barrel neck 12 when the distal piston 73 is pressed fully home in the barrel. The projection 74 has a duct 75 formed in the center thereof for receiving one end of a two-point needle penetrating the membrane.

The projection 74 serves to fill up the bulk of the barrel neck volume when the distal piston 73 is pressed fully home in the barrel 11 thus minimizing the amount of medicament left in the injection unit 70.

The distal piston 73 of FIG. 5 is suitable for use in the injection unit of the invention, but may also be otherwise used.

I claim:

1. A closure for an ampoule for an injection unit, said ampoule having a hollow, cylindrical barrel (11) with a distal end and a proximal end, said distal end terminating in a neck (12), an outwardly directed annular projection (30) on the neck, and a piston closing the proximal end of the barrel, said closure comprising:

a disc shaped part (31);

a holding cap comprising a proximal section in the form of a skirt (35;62) having one or more interior projections (38) at its proximal end for engagement behind the annular projection (30) of the barrel neck, and a distal section having means for attaching a needle thereto, the holding cap engaging the disc-shaped part (31) pressing it sealingly against the annular projection; and a locking ring (20;64) provided on the outside of the skirt (35;62) locking the projections (38) in their engagement position behind the annular projection (30), wherein the locking ring (20;64) and the skirt (35;62) are a pair of elements provided with mutually engaging means in the form of resilient fingers (37;65) on one of the elements, recesses (36;66) are provided behind the fingers in the element carrying the fingers to accommodate said fingers when the locking ring (20;64) is passed over the skirt (35;62), and an edge is provided on the other element not carrying the fingers (37;65) over which edge the fingers (37;65) grip irreversibly when the locking ring is mounted in a locking position on the skirt.

2. A closure according to claim 1, wherein the resilient fingers (37) are provided on the skirt (35) of the holding cap and are flexible outwardly protruding and disposed at a distance from the proximal end of the skirt, and the recesses (36) accommodating the fingers when the locking ring (20) is passed over the skirt, are provided in the skirt behind the fingers, and the edge over which the fingers may grip when the locking ring is mounted in position on the skirt is an upper edge of the locking ring (20).

3. A closure according to claim 2, wherein the holding cap has a number of slits formed in the proximal end of its skirt, and the fingers (37) are disposed at the distal end of said slits which serve as the recesses accommodating the fingers when the locking ring is passed over the skirt.

4. A closure according to claim 1, wherein the fingers (65) are provided inwardly protruding on the locking ring (64), the recesses (66) are provided as openings through the locking ring behind the fingers, and the skirt (62) of the holding cap is provided with other recesses (63) or openings each having an edge (67) over which the fingers (65) may grip.

* * * * *